United States Patent [19]

Corvers et al.

[11] Patent Number: 4,542,220

[45] Date of Patent: Sep. 17, 1985

[54] PREPARATION OF DERIVATIVES OF DICHLOROACETIC ACID ESTERS

[75] Inventors: Antonius Corvers, Beek; Joannes M. C. A. Mulders, Geleen, both of Netherlands

[73] Assignee: Stamicarbon B.V., Licensing Subsidiary of DSM, Geleen, Netherlands

[21] Appl. No.: 418,546

[22] Filed: Sep. 15, 1982

[30] Foreign Application Priority Data

Sep. 17, 1981 [NL] Netherlands .......................... 8104287

[51] Int. Cl.$^4$ .................. C07D 213/55; C07D 307/54; C07D 333/24; C07C 69/76
[52] U.S. Cl. ..................................... 546/341; 546/342; 549/79; 549/499; 560/8; 560/55; 560/105
[58] Field of Search ............................. 560/105, 55, 8; 546/341, 342; 549/79, 499

[56] References Cited

PUBLICATIONS

Bulletin De La Societe Chimique De France, 1959, pp. 850-853, Paris (France), M. Julia, et al., "Sur Quelques Derives Alpha–Chloro et Alpha, Alpha-Dichloroarylacetiques".

*Primary Examiner*—Alan L. Rotman
*Attorney, Agent, or Firm*—Cushman, Darby & Cushman

[57] ABSTRACT

The invention relates to a process for the preparation of derivatives of dichloroacetic acid esters, by reaction of a glyoxylic acid ester having the general formula $R_1$—CO—COOR$_2$, wherein $R_1$ represents an optionally substituted aryl or heteroaryl group and $R_2$ an alkyl, cycloalkyl or aryl group, with phosphoruspentachloride in the presence of a dispersant suitable for distributing the phosphoruspentachloride.

5 Claims, No Drawings

PREPARATION OF DERIVATIVES OF DICHLOROACETIC ACID ESTERS

BACKGROUND AND SUMMARY OF THE INVENTION

The invention relates to a process for the preparation of derivatives of dichloroacetic acid esters by reaction of the corresponding glyoxylic acid esters with phosphorus pentachloride.

Such a reaction has in the past been effected by allowing solid powdery phosphorus pentachloride to act on the corresponding glyoxylic acid ester (see Bull. soc. chim. de France 1959, pages 850-853). The desired product is then obtained at a yield of only the order of 45-55% of the theoretically possible yield.

The present invention provides a novel process by which the said reaction with phosphorus pentachloride can be effected to obtain a substantially higher yield.

The novel process according to this invention is for the preparation of derivatives of dichloroacetic acid ester, by reaction of the corresponding glyoxylic acid esters with phosphorus pentachloride, and is characterized in that a glyoxylic acid ester having the general formula $R_1$—CO—COOR$_2$, wherein $R_1$ represents an optionally substituted aryl or heteroaryl group and $R_2$ is an alkyl, cycloalkyl or aryl group, is reacted with the phosphorus pentachloride at a temperature of 35°-150° C., while in the presence of a liquid dispersant, suitable for distributing the phosphorus pentachloride through the reaction mixture, with the formation of the desired corresponding dichloro derivatives having the general formula $R_1$—CCl$_2$—COOR$_2$, wherein $R_1$ and $R_2$ have the above definitions.

By employing the process according to this invention the desired product can also be recovered from the reaction mixture at a sufficient level of purity such that the product recovered can be used for further applications without itself having to be distilled.

The reaction with phosphorus pentachloride according to this invention is exothermic. Therefore, in order to maintain the desired temperature, effective means for the removal of the heat of reaction must be employed. The desired reaction temperature is preferably maintained by using a liquid distributor having a boiling point corresponding with the desired reaction temperature. The heat of reaction can then be carried off by evaporation of the dispersant itself. The quantity of liquid dispersant present in the reaction mixture can be kept constant through application of suitable reflux condensation.

The reaction temperature may accordingly be varied within the above-stated limits; however, it is advantageous to maintain the temperature between 70° and 100° C.

In practicing the process according to this invention various dispersants suitable for distributing phosphorus pentachloride may be used, for instance alkanes or mixtures of alkanes, such as n-heptane and n-octane, cycloalkanes or mixtures of cycloalkanes, such as cyclopentane and cyclohexane, aromatics or mixtures of aromatics, such as benzene, toluene and xylenes and chlorinated hydrocarbons or mixtures of chlorinated hydrocarbons, such as chloroform, 1,2-dichloroethane and tetrachlorocarbon. Inorganic dispersants may also be employed such as, for instance, phosphorusoxytrichloride. The precise amount of the dispersant employed is not critical provided it is in sufficient quantity to effect complete distribution of the phosphorus pentachloride through the reaction mixture.

Various starting glyoxylic acid ester materials may be used. For instance, suitable compounds include those in which the group $R_1$ in the above general formula represents a phenyl, naphthyl, pyridyl, furyl or thienyl group, which groups may optionally be substituted with one or more substituents, e.g., of the class of Cl, $NO_2$, alkoxy with 1-8 C atoms and alkyl with 1-8 C atoms. As the $R_2$ group in these starting compounds an alkyl group with 1-8 C atoms, a cycloalkyl group with 5-8 C atoms in the ring, a phenyl group or a naphthyl group, for instance, may be used. These starting compounds can be very effectively prepared by the procedure described in copending U.S. application Ser. No. 320,562, filed Nov. 12, 1981 the disclosure of which is incorporated herein by reference.

The reaction mixture obtained according to this invention can, for instance, be worked up by distilling off the dispersant and the phosphorusoxytrichloride formed in the reaction, subsequently converting with water any phosphorus pentachloride still present into phosphoric acid and hydrogen chloride, separating the organic layer formed from the aqueous layer, washing the organic layer with water and, if desired, further purifying it by distillation. If in this working-up process the dispersant and the phosphorusoxytrichloride formed in the reaction process are not distilled off, an organic layer can be obtained which still contains the dispersant and which can be used as such for further conversions. The reaction mixture can be worked up also by distilling off the dispersant and phosphorusoxytrichloride formed and incorporating the still residue in an organic solvent from which any residual phosphorus pentachloride precipitates such as, for instance, cyclohexane. After separation removal of the phosphorus pentachloride an organic solution will be obtained from which the product obtained can be recovered by distillation if so desired.

The process according to this invention, in the application of which products can be obtained that can be used in, for instance, the preparation of pesticides, will now be further elucidated in the following examples.

EXAMPLE I

Cyclohexane (150 ml) and phosphorus pentachloride (220 g.) are introduced into a flask (capacity 1 liter), provided with a stirrer, reflux condenser, drop funnel and thermometer. The mixture is heated to about 90° C. (reflux temperature), at which point 164.7 g. phenylglyoxylic acid methylester is added in 40 minutes. After maintaining said rection conditions for 1.5 hours, gas chromatographic analysis shows that 99% of the quantity of glyoxylic acid ester is converted.

The cyclohexane is subsequently distilled off, the remaining reaction mixture is carefully poured out into one liter of water, and the mixture thus obtained extracted with ether. The organic layer is next washed with a saturated $NaHCO_3$ solution to a pH level of 8 and dried with magnesium sulphate. After evaporation of the ether, a residue (236.4 g.) remains which contains according to gas chromatographic analysis, 92% of the desired chlorinated ester.

The yield obtained is 93% of the theoretically possible yield. The boiling point of the product obtained is 95° C. at a pressure of 133 Pa.

EXAMPLE II

In the same manner as indicated in example I, 178 g. phenylglyoxylic acid ethylester is converted into the dichloro derivative, but with the use of 150 ml phosphorusoxytrichloride as the dispersant.

After a reaction time of 1 hour the phosphorusoxytrichloride is distilled off under reduced pressure, after which the product is worked up, as described.

This time the yield is 96% of the theoretically possible yield. The product boils at 147° C. at a pressure of $2.10^3$ Pa.

EXAMPLE III

Example I is repeated, but using 476 g. phosphorus pentachloride, 280 ml chloroform and 204.7 g. phenylglyoxylic acid butylester.

After a reaction time of 5.5 hours, the desired dichloroester is obtained at a yield of 89% of the theoretically possible yield. The product boils at 99°-100° C. at a pressure of 27 Pa.

COMPARATIVE EXAMPLE

In the same equipment as described in example I 20.6 g. phenylglyoxylic acid butylester with 41.6 g. powdery phosphorus pentachloride are heated together, but in the absence of a dispersant, to 80° C. Thereafter, the temperature of the reaction mixture rises to 170° C. Subsequently the reaction mixture is kept at 120° C. (boiling temperature) for an additional three hours. The reaction mixture is then worked up as described in example I.

The desired ester is here obtained at a yield of only 55% of the theoretically possible yield.

EXAMPLE IV

In the manner described in example I, 5.6 g. (p-methoxyphenyl)-glyoxylic acid ethylester in 5 ml cyclohexane is converted with 6.7 g. phosphorus pentachloride into a dichloro derivative.

After 2.5 hours the desired dichloroester is obtained at a yield of 94% of the theoretically possible yield. The product boils at 105°-107° C. at a pressure of 13 Pa.

EXAMPLE V

In equipment as described in example I 56 g. (2-thienyl)-glyoxylic acid ethylester is added dropwise to a boiling mixture of 65 ml cyclohexane and 90 g. phosphorus pentachloride in 10 minutes. After maintaining the reaction conditions for 4 hours, the reaction mixture is cooled and worked up as follows:

Under reduced pressure the cyclohexane and the phosphorusoxytrichloride formed are distilled off, and the still residue is then incorporated in cyclohexane. The phosphoruspentachloride thus precipitated is filtered off and subsequently pyridine is added dropwise during stirring (which binds the phosphoruspentachloride still dissolved) to the filtrate until no further precipitate is formed. After the precipitate has been filtered off and the solvent has been distilled off under reduced pressure, 71 g. crude product is obtained containing 92% of the desired chlorinated ester. The yield is 90% of the theoretically possible yield. The product boils at 95° C. at a pressure of 40 Pa.

The products obtained in these examples I–V are suitable for further use without requiring a distillation of the same. Other glyoxalic acid esters, as described above, may be employed as starting materials in processes according to the foregoing Examples with similar results.

In general the amount of phosphorus pentachloride used should be at a mol ratio of 1 to 2.5 with respect to the amount of glyoxylic acid ester employed.

What we claim is:

1. A process for prepring dichloroacetic acid ester compounds, comprising reacting a glyoxylic acid ester derivative of formula $$R_1-CO-COOR_2,$$

wherein
  $R_1$ is selected from the group consisting of phenyl, naphthyl, pyridyl, furyl, and thienyl, and wherein said $R_1$ may be substituted with Cl, $NO_2$, alkyl having 1–8 C atoms, or alkoxy having 1–8 C atoms, and wherein
  $R_2$ is selected from the group consisting of alkyl having 1–8 C atoms, cycloalkyl having 5–8 C atoms, phenyl, and naphthyl,
  with phosphorus pentachloride
  in a dispersant selected from the group consisting of cyclohexane, chloroform and phosphorousoxychloride, suitable for distributing said phosphorus pentachloride, and
  at a temperature of from 35° to 150° C.
to form the corresponding dichloroacetic ester compound having the formula, $$R_1-CCl_2-COOR_2.$$

2. A process according to claim 1 wherein said reaction temperature is from 70° to 100° C.

3. A process according to claim 1 or claim 2, wherein said reaction temperature is maintained by employing a dispersant having a boiling point corresponding to the desired reaction temperature and maintaining reflex conditions.

4. A process according to claim 1 or claim 2 wherein $R_1$ represents a phenyl, napthyl, pyridyl, furyl or thienyl group or such group carrying a substituent of the class of Cl, NO2, and alkoxy or alkyl having up to 8 carbon atoms.

5. A process according to claim 1 or claim 2 wherein $R_1$ represents a phenyl, napthyl, pyridyl, furyl or thienyl group or such group carrying a substituent of the class of Cl, NO2, and alkoxy or alkyl having up to 8 carbon atoms and wherein $R_2$ represents an alkyl group of up to 8 carbon atoms, a cycloalkyl group of from 5 to 8 ring carbon atoms, a phenyl group or a naphthyl group.

* * * * *